United States Patent [19]
Trinh et al.

[11] Patent Number: 5,714,137
[45] Date of Patent: Feb. 3, 1998

[54] UNCOMPLEXED CYCLODEXTRIN SOLUTIONS FOR ODOR CONTROL ON INANIMATE SURFACES

[75] Inventors: Toan Trinh, Maineville; Jerome Paul Cappel, Cincinnati; Philip Anthony Geis, West Chester; Mark Lee McCarty, Loveland; David Pilosof, Cincinnati; Susan Schmaedecke Zwerdling, Wyoming, all of Ohio

[73] Assignee: The Procter & Gamble Company, Cincinnati, Ohio

[21] Appl. No.: 289,734

[22] Filed: Aug. 12, 1994

[51] Int. Cl.$^6$ .................................................. A61L 9/01
[52] U.S. Cl. .................... 424/76.4; 424/76.1; 424/76.21; 252/8.6; 252/8.7; 252/8.75; 252/8.8; 252/8.9
[58] Field of Search ........................ 424/76.1, 76.8, 424/76.2; 252/8.6, 8.7, 8.75, 8.8, 8.9

[56] References Cited

U.S. PATENT DOCUMENTS

| | | | |
|---|---|---|---|
| D. 244,991 | 7/1977 | Weckman et al. | D9/63 |
| D. 275,078 | 8/1984 | Wassergord et al. | D9/300 |
| D. 277,978 | 3/1985 | Bundschuh | D23/17 |
| 2,544,093 | 3/1951 | Kilgore | 252/1 |
| 3,074,891 | 1/1963 | Kulka | 252/305 |
| 3,172,817 | 3/1965 | Leupold et al. | 167/90 |
| 3,426,011 | 2/1969 | Parmerter et al. | 260/209 |
| 3,436,776 | 4/1969 | Davis | 9/8 |
| 3,453,257 | 7/1969 | Parmerter et al. | 260/209 |
| 3,453,258 | 7/1969 | Parmerter et al. | 260/209 |
| 3,453,259 | 7/1969 | Parmerter et al. | 260/209 |
| 3,453,260 | 7/1969 | Parmerter et al. | 260/209 |
| 3,459,731 | 8/1969 | Gramera et al. | 260/209 |
| 3,553,191 | 1/1971 | Parmerter et al. | 260/209 |
| 3,565,887 | 2/1971 | Parmerter et al. | 260/234 |
| 3,600,325 | 8/1971 | Kaufman et al. | 252/305 |
| 4,082,223 | 4/1978 | Nozawa | 239/333 |
| 4,161,288 | 7/1979 | McKinney | 239/333 |
| 4,265,899 | 5/1981 | Lewis et al. | 424/270 |
| 4,267,166 | 5/1981 | Yajima | 424/48 |
| 4,274,560 | 6/1981 | Cater | 222/321 |
| 4,325,939 | 4/1982 | Shah | 424/55 |
| 4,434,917 | 3/1984 | Saito et al. | 222/383 |
| 4,449,987 | 5/1984 | Lindauer | 44/7.5 |
| 4,469,674 | 9/1984 | Shah et al. | 424/52 |
| 4,535,152 | 8/1985 | Szejtli et al. | 536/103 |
| 4,558,821 | 12/1985 | Tada et al. | 239/333 |
| 4,616,008 | 10/1986 | Hirai et al. | 514/200 |
| 4,638,058 | 1/1987 | Brandt et al. | 536/103 |
| 4,678,598 | 7/1987 | Ogino et al. | 252/174.17 |
| 4,693,890 | 9/1987 | Wilson et al. | 424/78 |
| 4,696,676 | 9/1987 | Wilson et al. | 44/7.5 |
| 4,727,824 | 3/1988 | Ducharme et al. | 119/1 |
| 4,735,347 | 4/1988 | Schultz et al. | 222/321 |
| 4,746,734 | 5/1988 | Tsuchiyama et al. | 536/103 |
| 4,779,803 | 10/1988 | Corsette | 239/428.5 |
| 4,818,524 | 4/1989 | Gibbs | 424/76.1 |
| 4,819,835 | 4/1989 | Tasaki | 222/383 |
| 4,895,279 | 1/1990 | Schultz | 222/321 |
| 4,933,371 | 6/1990 | Hink et al. | 514/739 |
| 4,946,672 | 8/1990 | Gibbs | 424/76.1 |
| 5,094,761 | 3/1992 | Trinh et al. | 252/8.9 |
| 5,102,564 | 4/1992 | Gardlik et al. | 252/8.9 |
| 5,111,971 | 5/1992 | Winer | 222/95 |
| 5,196,200 | 3/1993 | Wilson et al. | 424/411 |
| 5,207,933 | 5/1993 | Trinh et al. | 252/8.6 |
| 5,232,126 | 8/1993 | Winer | 222/95 |
| 5,234,610 | 8/1993 | Gardlik et al. | 252/8.6 |
| 5,234,611 | 8/1993 | Trinh et al. | 252/8.8 |
| 5,303,867 | 4/1994 | Peterson | 239/333 |
| 5,429,628 | 7/1995 | Trinh et al. | 604/359 |

FOREIGN PATENT DOCUMENTS

| | | | |
|---|---|---|---|
| 53-041440-A | 4/1978 | Japan | A61K 7/32 |
| 53-41440 | 4/1978 | Japan | A61K 7/32 |
| 58-124452 | 7/1983 | Japan | A61L 9/01 |
| 61-128973 | 6/1986 | Japan | A61L 9/01 |
| 63-164953 | 7/1988 | Japan . | |
| 01256596A | 10/1989 | Japan | C11D 3/38 |
| 1-256597 | 10/1989 | Japan . | |
| 02251681A | 10/1990 | Japan . | |
| 03170415A | 7/1991 | Japan | A61K 7/32 |
| 3-170415 | 7/1991 | Japan | A61K 7/32 |
| 3-284616 | 12/1991 | Japan | A61K 7/16 |
| 941105 | 11/1963 | United Kingdom . | |
| 89/02698 | 4/1989 | WIPO | A01K 1/015 |
| 91/12029 | 8/1991 | WIPO | A61L 9/01 |

OTHER PUBLICATIONS

"Semio Activity of Flavor and Fragrance Molecules on Various Insect Species", B. D. Mookherjee, et al., *Bioactive Volatile Compounds from Plants*, 1993 ACS Symposium Series, pp. 35-48.

Formation of Inclusion Complex between Cyclodextrin and d-Limonese by a Twin Screw Kneader, T. Furuta, et al., Department of Biotechnology Tottori University.

Effects of Water and Alcohol on the formation of inclusion complexes of d-limonene and cyclodextrins, T. Furuta, et al., *Supramolecular Chemistry*, vol. 1, pp. 321-325.

Studies on the Industrial Production and Application of Cyclodextrins, *Denpun Kagaku*, vol. 36, No. 1, pp. 35-42 (1989).

(List continued on next page.)

*Primary Examiner*—Amy Hulina
*Attorney, Agent, or Firm*—Robert B. Aylor

[57] ABSTRACT

The present invention relates to a stable, aqueous odor-absorbing composition, for use on inanimate surfaces. The composition comprises from about 0.1% to about 5%, by weight of the composition, of solubilized, water-soluble, uncomplexed cyclodextrin, an effective amount of a solubilized, water-soluble, antimicrobial preservative having a water-solubility of greater than about 0.3%, optional perfume, and an aqueous carrier.

The composition is essentially free of any material that would soil or stain fabric and has a pH of greater than about 3. The composition can be incorporated into a spray dispenser to create an article of commerce that can facilitate treatment of articles and/or surfaces with uncomplexed cyclodextrin solutions of a level that is effective yet is not discernible when dried on the surface.

31 Claims, No Drawings

OTHER PUBLICATIONS

Application of Cyclodextrins to Foods, Toiletries and Other Products in Japan, H. Hashimoto, Ensuiko Sugar Refining Co.

Interaction between Preservatives and 2–Hydroxypropyl–β–Cyclodextrin, T. Loftsson, et al., *Drug Development and Industrial Pharmacy*, 18(13), 1477–1484, (1992).

Interactions between p–hydroxybenzoic acid esters and hydroxypropyl–β–cyclodextrin and their antimicrobial effect against *Candida albicans*, S. J. Lehner, et al., Department of Pharmaceutics and Biopharmaceutics, Christian Albrecht University, (1992).

Powdery Encapsulation of d–Limonese by Kneading with Mixed Powders of β–Cyclodextrin and Maltodextrin at Low Water Content, T. Furuta, et al., Department of Biotechnology Tottori University, Sep. 21, 1993.

Effect of Hydroxypropyl–β–cyclodextrin on the Antimicrobial Action of Preservatives, S. J. Lehner, et al., *J. Pharm. Pharmacol*, 1994, 46: 186–191.

Optimal Performances with Minimal Chemical Modifications of Cyclodextrins, F. Djedaini–Pilard et al., CEA, Service de Chimie Moléculaire, CE de Saclay, F–91191 Gif sur Yvette, France.

UNCOMPLEXED CYCLODEXTRIN SOLUTIONS FOR ODOR CONTROL ON INANIMATE SURFACES

TECHNICAL FIELD

The present invention relates to stable, preferably clear, aqueous odor-absorbing compositions (solutions), articles of manufacture, and/or methods of use, not including use directly on human skin, comprising solubilized water-soluble uncomplexed cyclodextrin and, preferably, a water-soluble antimicrobial preservative for said aqueous cyclodextrin solution. The odor-absorbing compositions are designed to control odors caused by a broad spectrum of organic odoriferous materials, which may, or may not, contain reactive functional groups, and to preferably remain shelf stable for a substantial period of time. Preferably, the aqueous odor-absorbing composition is for use on inanimate surfaces, especially fabrics, and more specifically, clothes, in order to restore and/or maintain freshness by reducing malodor without the need for washing or dry cleaning.

BACKGROUND OF THE INVENTION

The present invention relates to stable, preferably clear, aqueous odor absorbing compositions, articles of manufacture and/or method for use on surfaces, not including use directly on human skin, as an odor-absorbing composition. Such compositions can optionally provide a "scent signal" in the form of a pleasant odor which signals the removal of the malodor. Preferably, the compositions are sprayed onto fabrics, particularly clothes, to restore their freshness by reducing malodor without washing or dry cleaning. The compositions are preferably not used directly on human skin because the preferred preservative may cause skin irritation. Fabrics treated with some preferred compositions of the present invention can also optionally provide release of fragrance upon rewetting, such as when the wearer perspires. This phenomenon provides an added benefit to fabrics treated with the composition of the present invention in that the fabrics will stay freshet longer.

A wide variety of deodorizing compositions are known in the art, the most common of which contain perfumes to mask malodor. Odor masking is the intentional concealment of one odor by the addition of another. The control of odor on fabrics, in particular clothes, has been accomplished by using perfumes, colognes, etc. However, preference to perfume is greatly varied and high levels are needed to ensure that the malodor is no longer noticeable.

Odor modification, in which the odor is changed, e.g., by chemical modification, has also been used. Current malodor modification methods known in the art are oxidative degradation, which uses oxidizing agents such as oxygen bleaches, chlorine, chlorinated materials such as sodium hypochlorite, chlorine dioxide, etc., and potassium permanganate to reduce malodor, and reductive degradation which uses reducing agents such as sodium bisulfite to reduce malodor. Both of these methods are unacceptable for general use on fabric because they can damage colored fabrics, specifically, they can bleach and/or discolor colored fabrics.

Other methods of odor control utilize actives that are targeted to react with malodors having specific chemical functional groups. Examples of such actives are; biguanide polymers, which complex with organic compounds containing organically bound N and/or S atoms and fatty alcohol esters of methyl methacrylic acid which react with thiols, amines, and aldehydes. Such actives are limited in the scope of protection which they afford because they only react with limited types of malodor. A more detailed description of these methods can be found in U.S. Pat. Nos. 2,544,093; 3,074,891; 4,818,524; and 4,946,672; and U.K. Pat. App. No. 941,105, all of said patents and applications incorporated herein by reference.

Other types of deodorizing compositions known in the art contain antibacterial and antifungal agents which regulate the malodor-producing microorganisms found on the surface to which the deodorizing composition is directed. Many skin deodorant products use this technology. These compositions are not effective on malodors that have already been produced and malodors that do not come from bacterial sources, such as tobacco or food odors.

Fabric malodor is most commonly caused by environmental odors such as tobacco odor, cooking and/or food odors, or body odor. The unpleasant odors are mainly organic molecules which have different structures and functional groups, such as amines, acids, alcohols, aldehydes, ketones, phenolics, polycyclics, indoles, aromatics, polyaromatics, etc. They can also be made up of sulfur-containing functional groups, such as, thiol, mercaptan, sulfide and/or disulfide groups.

It is preferable to apply an odor absorbing material, preferably a broad spectrum odor absorbing material, to fabrics rather than a masking or chemical reaction material for odor control between washing and dry cleaning operations. As opposed to a masking or chemical reaction material, odor absorbing material can eliminate a broad spectrum of odoriferous molecules and usually does not contribute an odor of its own. The commonly known solid odor absorbers such as activated charcoal and zeolites can be harmful to fabrics and therefore are not preferred as an odor controlling agent under these circumstances. Activated charcoal easily stains light colored fabrics and zeolites are seen as a light colored stain on dark colored fabrics. Furthermore, the zeolites can cause a "harsh" feel if too much is deposited.

Uncomplexed cyclodextrin molecules, which are made up of varying numbers of glucose units provide the absorbing advantages of known absorbent deodorizing compositions without harmful effects to fabrics. The current teachings in the art suggest that cyclodextrin does not contribute to the growth of microorganisms despite the fact that they are made up of varying numbers of glucose units. See *Effect of Hydroxypropyl-B-cyclodextrin on the Antimicrobial Action of Preservatives*, S. J. Lehner, B. W. Müller and J. K. Seydel, J. Pharm. Pharmacol 1994, 46:p.188 and *Interactions Between P-Hydroxybenzoic acid Esters and Hydroxypropyl-B-Cyclodextrin and Their Antimocrobial Effect Against Candida Albicans*, S. J. Lehner, B. W. Müller and J. K. Seydel, International Journal of Pharmaceuties, 1993, 93, pp. 201–208. It has been discovered, however, that cyclodextrin is a prime breeding ground for certain microorganisms, especially when in aqueous compositions. This growth problem leads to a problem with storage stability of cyclodextrin solutions for any significant length of time. Contamination by certain microorganisms, can cause microbial growth resulting in an unsightly and/or malodorous solution. Because microbial growth in cyclodextrin solutions can occur, it is preferable to include a water-soluble antimicrobial preservative, which is effective for inhibiting and/or regulating microbial growth, to increase storage stability of clear, aqueous odor-absorbing solutions containing water-soluble cyclodextrin.

SUMMARY OF THE INVENTION

The present invention relates to a stable, aqueous odor-absorbing composition, for use on inanimate surfaces, comprising:

A. from about 0.1% to about 5%, by weight of the composition, of solubilized, water-soluble, uncomplexed cyclodextrin;

B. an effective amount of a solubilized, water-soluble, antimicrobial preservative having a water solubility of greater than about 0.3%;

C. optional perfume; and

D. an aqueous carrier; and wherein said composition is essentially free of any material that would soil or stain fabric and has a pH of greater than about 3.

The composition can be incorporated into a spray dispenser to create an article of commerce that can facilitate treatment of articles and/or surfaces with uncomplexed cyclodextrin solutions of a level that is effective yet is not discernible when dried on the surface.

DETAILED DESCRIPTION OF THE INVENTION

The present invention relates to a stable, aqueous odor-absorbing composition, for use on inanimate surfaces, comprising:

A. from about 0.1% to about 5%, by weight of the composition, of solubilized, water-soluble, uncomplexed cyclodextrin;

B. an effective amount of a solubilized, water-soluble, antimicrobial preservative having a water solubility of greater than about 0.3%;

C. optional perfume; and

D. an aqueous carrier; and wherein said composition is essentially free of any material that would soil or stain fabric and has a pH of greater than about 3.

I. COMPOSITION

(A) CYCLODEXTRIN

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms; therefore, this surface is fairly hydrophobic. The unique shape and physical-chemical properties of the cavity enable the cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may, or may not, contain reactive functional groups. The complexation between cyclodextrin and odorous molecules occurs rapidly in the presence of water. However, the extent of the complex formation also depends on the polarity of the absorbed molecules. In an aqueous solution, strongly hydrophilic molecules (those which are highly water-soluble) are only partially absorbed, if at all. Therefore, cyclodextrin does not complex effectively with some very low molecular weight organic amines and acids when they are present at low levels on wet fabrics. As the water is being removed however, e.g., the fabric is being dried off, some low molecular weight organic amines and acids have more affinity and will complex with the cyclodextrins more readily.

The cavities within the cyclodextrin in the solution of the present invention should remain essentially untilled (the cyclodextrin remains uncomplexed) while in solution, in order to allow the cyclodextrin to absorb various odor molecules when the solution is applied to a surface. Non-derivatised (normal) beta-cyclodextrin can be used although it is not preferred due to its low solubility, especially in compositions which call for a level of cyclodextrin higher than its water solubility at room temperature (about 1.85 grams in 100 grams of water). Non-derivatised beta-cyclodextrin is further not preferred when the composition contains optional perfume material and a clear solution is preferred. When non-derivatised beta-cyclodextrin is used in either of these situations the aqueous solution becomes cloudy and is not clear. Not to be limited by theory, it is believed that some beta-cyclodextrin and/or beta-cyclodextrin/perfume complexes solidify and/or precipitate out producing an undesirable cloudy aqueous solution.

Preferably, the odor absorbing solution of the present invention is clear. The term "clear" as defined herein means transparent or translucent, preferably transparent as in "water clear," when observed through a layer having a thickness of less than about 10 cm.

Preferably, the cyclodextrins used in the present invention are highly water-soluble such as, alpha-cyclodextrin and derivatives thereof, gamma-cyclodextrin and derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a $^-CH_2$—CH(OH)—$CH_3$ or a $^-CH_2CH_2$—OH group; branched cyclodextrins such as maltose-bonded cyclodextrins; cationic cyclodextrins such as those containing 2-hydroxy-3(dimethylamino) propyl ether, wherein R is $CH_2$—CH(OH)—$CH_2$—N$(CH_3)_2$ which is cationic at low pH; quaternary ammonium, e.g., 2-hydroxy-3-(trimethylammonio)propyl ether chloride groups, wherein R is $CH_2$—CH(OH)—$CH_2$—N$^+(CH_3)_3$Cl$^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, herein incorporated by reference; and mixtures thereof. Other cyclodextrin derivatives are disclosed in U.S. Pat. No: 3,426,011, Parmerter et al., issued Feb. 4, 1969; U.S. Pat. Nos. 3,453,257; 3,453,258; 3,453,259; and 3,453, 260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. The availability of solubilized, uncomplexed cyclodextrins is essential for an effective and efficient odor control performance. Solubilized, water-soluble cyclodextrin can exhibit more efficient odor control performance than non-water-soluble cyclodextrin when deposited onto surfaces, especially fabric.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available, methylated beta-cyclodextrin is a randomly methylated beta-cyclodextrin having a degree of substitution of about 12.6. The preferred cyclodextrins are available, e.g., from American Maize-Products Company and Wacker Chemicals (U.S.A), Inc.

It is also preferable to use a mixture of cyclodextrins. Such mixtures absorb odors more broadly by complexing with a wider range of odoriferous molecules having a wider range of molecular sizes. Preferably at least a portion of the cyclodextrins is alpha-cyclodextrin or its derivatives thereof, gamma-cyclodextrin or its derivatives thereof, and/or derivatised beta-cyclodextrin, more preferably a mixture of alpha-cyclodextrin, or an alpha-cyclodextrin derivative, and derivatised beta-cyclodextrin, even more preferably a mixture of derivatised alpha-cyclodextrin and derivatised beta-cyclodextrin, most preferably a mixture of hydroxypropyl alpha-cyclodextrin and hydroxypropyl beta-cyclodextrin, and/or a mixture of methylated alpha-cyclodextrin and methylated beta-cyclodextrin.

For controlling odor on fabrics, the composition is preferably used as a spray. It is preferable that the composition of the present invention contain low levels of cyclodextrin so that a visible stain does not appear on the fabric at normal usage levels. Preferably, the solution is virtually not discernible when dry. Typical levels of cyclodextrin are from about 0.1% to about 5%, preferably from about 0.2% to about 4%, more preferably from about 0.3% to about 3%, most preferably from about 0.4% to about 2%. Compositions with higher concentrations can leave unacceptable visible stains on fabrics as the solution evaporates off of the fabric. This is especially a problem on thin, colored, synthetic fabrics. In order to avoid or minimize the occurrence of fabric staining, it is preferable that the fabric be treated at a level of less than about 5 mg of cyclodextrin per mg of fabric, more preferably less than about 2 mg of cyclodextrin per mg of fabric.

Concentrated compositions can also be used in order to provide a less expensive product. When a concentrated product is used, i.e., when the level of cyclodextrin used is from about 3% to about 5%, it is preferable to dilute the composition before treating fabrics in order to avoid staining. Preferably the cyclodextrin is diluted with about 50% to about 2000%, more preferably with about 60% to about 1000%, most preferably with about 75% to about 500% by weight of the composition of water.

(B) ANTIMICROBIAL PRESERVATIVE

Cyclodextrin molecules are made up of varying numbers of glucose units which can make them a prime breeding ground for certain microorganisms, especially when in aqueous compositions. This problem, that certain organisms grow extremely well on cyclodextrin, has not been previously disclosed. This drawback can lead to the problem of storage stability of cyclodextrin solutions for any significant length of time. Contamination by certain microorganisms with subsequent microbial growth can result in an unsightly and/or malodorous solution. Because microbial growth in cyclodextrin solutions is highly objectionable when it occurs, it is highly preferable to include a solubilized water-soluble, antimicrobial preservative, which is effective for inhibiting and/or regulating microbial growth in order to increase storage stability of the preferably clear, aqueous odor-absorbing solution containing water-soluble cyclodextrin.

Typical microorganisms that can be found in cyclodextrin supplies and whose growth can be found in the presence of cyclodextrin in aqueous cyclodextrin solutions include bacteria, e.g., *Bacillus thuringiensis* (cereus group) and *Bacillus sphaericus*; and fungi, e.g., *Aspergillus ustus*. *Bacillus sphaericus* is one of the most numerous members of Bacillus species in soils. *Aspergillus ustus* is common in grains and flours which are raw materials to produce cyclodextrins. Microorganisms such as *Escherichia coil* and *Pseudomonas aeruginosa* are found in some water sources, and can be introduced during the preparation of cyclodextrin aqueous solutions.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used.

Antimicrobial preservatives useful in the present invention include biocidal compounds, i.e., substances that kill microorganisms, or biostatic compounds, i.e., substances that inhibit and/or regulate the growth of microorganisms.

Preferred antimicrobial preservatives are those that are water-soluble and are effective at low levels because the organic preservatives can form inclusion complexes with the cyclodextrin molecules and compete with the malodorous molecules for the cyclodextrin cavities, thus rendering the cyclodextrins ineffective as odor controlling actives. Water-soluble preservatives useful in the present invention are those that have a solubility in water of at least about 0.3 g per 100 ml of water, i.e., greater than about 0.3% at room temperature, preferably greater than about 0.5% at room temperature. These types of preservatives have a lower affinity to the cyclodextrin cavity, at least in the aqueous phase, and are therefore more available to provide antimicrobial activity. Preservatives with a water-solubility of less than about 0.3% and a molecular structure that readily fits into the cyclodextrin cavity, have a greater tendency to form inclusion complexes with the cyclodextrin molecules, thus rendering the preservative less effective to control microbes in the cyclodextrin solution. Therefore, many well known preservatives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with cyclodextrin.

The water-soluble antimicrobial preservative in the present invention is included at an effective amount. The term "effective amount" as herein defined means a level sufficient to prevent spoilage, or prevent growth of inadvertently added microorganisms, for a specific period of time. In other words, the preservative is not being used to kill microorganisms on the surface onto which the composition is deposited in order to eliminate odors produced by microorganisms. Instead, it is preferably being used to prevent spoilage of the cyclodextrin solution in order to increase the shelf-life of the composition. Preferred levels of preservative are from about 0.0001% to about 0.5%, more preferably from about 0.0002% to about 0.2%, most preferably from about 0.0003% to about 0.1%, by weight of the composition.

In order to reserve most of the cyclodextrins for odor control, the cyclodextrin to preservative molar ratio should be greater than about 5:1, preferably greater than about 10:1, more preferably greater than about 50:1, even more preferably greater than about 100:1.

The preservative can be any organic preservative material which will not cause damage to fabric appearance, e.g., discoloration, coloration, bleaching. Preferred water-soluble preservatives include organic sulfur compounds, halogenated compounds, cyclic organic nitrogen compounds, low molecular weight aldehydes, quaternary ammonium compounds, dehydroacetic acid, phenyl and phenoxy compounds, and mixtures thereof.

The following are non-limiting examples of preferred water-soluble preservatives for use in the present invention.

(1) Organic Sulfur Compounds

Preferred water-soluble preservatives for use in the present invention are organic sulfur compounds. Some non-limiting examples of organic sulfur compounds suitable for use in the present invention are:

(a) 3-Isothiazolone Compounds

A preferred preservative is an antimicrobial, organic preservative containing 3-isothiazolone groups having the formula:

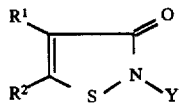

wherein

Y is an unsubstituted alkyl, alkenyl, or alkynyl group of from about 1 to about 18 carbon atoms, an unsubstituted or substituted cycloalkyl group having from about a 3 to about a 6 carbon ring and up to 12 carbon atoms, an unsubstituted or substituted aralkyl group of up to about 10 carbon atoms, or an unsubstituted or substituted aryl group of up to about 10 carbon atoms;

$R^1$ is hydrogen, halogen, or a ($C_1$–$C_4$) alkyl group; and $R^2$ is hydrogen, halogen, or a ($C_1$–$C_4$) alkyl group.

Preferably, when Y is methyl or ethyl, $R^1$ and $R^2$ should not both be hydrogen. Salts of these compounds formed by reacting the compound with acids such as hydrochloric, nitric, sulfuric, etc. are also suitable.

This class of compounds is disclosed in U.S. Pat. No. 4,265,899, Lewis et al., issued May 5, 1981, and incorporated herein by reference. Examples of said compounds are: 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; 5-chloro-2-methyl-3-isothiazolone; 2-methyl-4-isothiazolin-3-one; and mixtures thereof. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company.

When Kathon® is used as the preservative in the present invention it is typically present at a level of from about 0.0001% to about 0.01%, preferably from about 0.0002% to about 0.005%, more preferably from about 0.0003% to about 0.003%, most preferably from about 0.0004% to about 0.002%, by weight of the composition.

(b) Sodium Pyrithione

Another preferred organic sulfur preservative is sodium pyrithione, with water solubility of about 50%. When sodium pyrithione is used as the preservative in the present invention it is typically present at a level of from about 0.0001% to about 0.01%, preferably from about 0.0002% to about 0.005%, more preferably from about 0.0003% to about 0.003%, by weight of the composition.

Mixtures of the preferred organic sulfur compounds can also be used as the preservative in the present invention.

(2) Halogenated Compounds

Preferred preservatives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water. When Bronidox is used as the preservative in the present invention it is typically present at a level of from about 0.0005% to about 0.02%, preferably from about 0.001% to about 0.01%, by weight of the composition;

2-bromo-2-nitropropane-1,3-diol, available under the trade name Bronopol® from Inolex can be used as the preservative in the present invention. Bronopol has a solubility of about 25% in water. When Bronopol is used as the preservative in the present invention it is typically present at a level of from about 0.002% to about 0.1%, preferably from about 0.005% to about 0.05%, by weight of the composition;

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water. When chlorohexidine is used as the preservative in the present invention it is typically present at a level of from about 0.0001% to about 0.04%, preferably from about 0.0005% to about 0.01%, by weight of the composition.

1,1,1-Trichloro-2-methylpropan-2-ol, commonly known as chlorobutanol, with water solubility of about 0.8%; a typical effective level of chlorobutanol is from about 0.1% to about 0.5%, by weight of the composition.

4,4'-(Trimethylenedioxy)bis-(3-bromobenzamidine) diisethionate, or dibromopropamidine, with water solubility of about 50%; when dibromopropamidine is used as the preservative in the present invention it is typically present at a level of from about 0.0001% to about 0.05%, preferably from about 0.0005% to about 0.01% by weight of the composition.

Mixtures of the preferred halogenated compounds can also be used as the preservative in the present invention.

(3) Cyclic Organic Nitrogen Compounds

Preferred water-soluble preservatives for use in the present invention are cyclic organic nitrogen compounds. Some non-limiting examples of cyclic organic nitrogen compounds suitable for use in the present invention are:

(a) Imidazolidinedione Compounds

Preferred preservatives for use in the present invention are imidazolidione compounds. Some non-limiting examples of imidazolidinedione compounds suitable for use in the present invention are:

1,3-bis(hydroxymethyl)-5,5-dimethyl-2,4-imidazolidinedione, commonly known as dimethyloldimethylhydantoin, or DMDM hydantoin, available as, e.g., Glydant® from Lonza. DMDM hydantoin has a water solubility of more than 50% in water, and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza. When Glydant Plus® is used as the preservative in the present invention, it is typically present at a level of from about 0.005% to about 0.2%;

N-[1,3-bis(hydroxymethyl)2,5-dioxo-4-imidazolidinyl]-N,N'-bis(hydroxymethyl) urea, commonly known as diazolidinyl urea, available under the trade name Germall II® from Sutton Laboratories, Inc. (Sutton) can be used as the preservative in the present invention. When Germall II® is used as the preservative in the present invention, it is typically present at a level of from about 0.01% to about 0.1%;

N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from (Sutton) can be used as the preservative in the present invention. When imidazolidinyl urea is used as the preservative, it is typically present at a level of from about 0.05% to about 0.2%, by weight of the composition.

Mixtures of the preferred imidazolidinedione compounds can also be used as the preservative in the present invention.

(b) Polymethoxy Bicyclic Oxazolidine

Another preferred water-soluble cyclic organic nitrogen preservative is polymethoxy bicyclic oxazolidine, having the general formula:

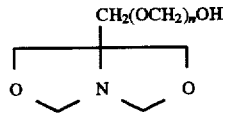

where n has a value of from about 0 to about 5, and is available under the trade name Nuosept® C from Hüls America. When Nuosept® C is used as the preservative, it is typically present at a level of from about 0.005% to about 0.1%, by weight of the composition.

Mixtures of the preferred cyclic organic nitrogen compounds can also be used as the preservative in the present invention.

(4) Low Molecular Weight Aldehydes (a) Formaldehyde

A preferred preservative for use in the present invention is formaldehyde. Formaldehyde is a broad spectrum preservative which is normally available as formalin which is a 37% aqueous solution of formaldehyde. When formaldehyde is used as the preservative in the present invention, typical levels are from about 0.003% to about 0.2%, preferably from about 0.008% to about 0.1%, more preferably from about 0.01% to about 0.05%, by weight of the composition.

(b) Glutaraldehyde

A preferred preservative for use in the present invention is glutaraldehyde. Gutaraldehyde is a water-soluble, broad spectrum preservative commonly available as a 25% or a 50% solution in water. When glutaraldehyde is used as the preservative in the present invention it is typically present at a level of from about 0.005% to about 0.1%, preferably from about 0.01% to about 0.05%, by weight of the composition.

(5) Quaternary Compounds

Preferred preservatives for use in the present invention are cationic and/or quaternary compounds. Such compounds include polyaminopropyl biguanide, also known as polyhexamethylene biguanide having the general formula:

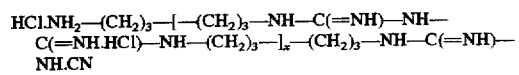

Polyaminopropyl biguanide is a water-soluble, broad spectrum preservative which is available as a 20% aqueous solution available under the trade name Cosmocil CQ® from ICI Americas, Inc., or under the trade name Mikrokill® from Brooks, Inc.

1-(3-Chlorallyl)-3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred.

Mixtures of the preferred quaternary ammonium compounds can also be used as the preservative in the present invention.

When quaternary ammonium compounds are used as the preservative in the present invention, they are typically present at a level of from about 0.005% to about 0.2%, preferably from about 0.01% to about 0.1%, by weight of the composition.

(6) Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative. When dehydroacetic acid is used as the preservative it is typically used at a level of from about 0.005% to about 0.2%, preferably from about 0.008% to about 0.1%, more preferably from about 0.01% to about 0.05%, by weight of the composition.

(7) Phenyl and Phenoxy Compounds

Some non-limiting examples of phenyl and phenoxy compounds suitable for use in the present invention are:

4,4'-diamidino-α,ω-diphenoxypropane diisethionate, commonly known as propamidine isethionate, with water solubility of about 16%; and 4,4'-diamidino-α,ω-diphenoxyhexane diisethionate, commonly known as hexamidine isethionate. Typical effective level these salts is about 0.0002% to about 0.05%.

Other examples are benzyl alcohol, with a water solubility of about 4%; 2-phenylethanol, with a water solubility of about 2%; and 2-phenoxyethanol, with a water solubility of about 2.67%; typical effective level of these phenyl and phenoxy alcohol is from about 0.1% to about 0.5%, by weight of the composition.

(8) Mixtures thereof

The preservatives of the present invention can be used in mixtures in order to control a broad range of microorganisms.

Bacteriostatic effects can sometimes be obtained for aqueous compositions by adjusting the composition pH to an acid pH, e.g., less than about pH 4, preferably less than about pH 3, or a basic pH, e.g., greater than about 10, preferably greater than about 11. Low pH for microbial control is not a preferred approach in the present invention because the low pH can cause chemical degradation of the cyclodextrins. High pH for microbial control is also not preferred because at high pH's, e.g., greater than about 10, preferably greater than about 11, the cyclodextrins can be ionized and their ability to complex with organic materials is reduced. Therefore, aqueous compositions of the present invention should have a pH of from about 3 to about 10, preferably from about 4 to about 8, more preferably from about 4.5 to about 7.

As stated above, it is preferable to use the preservative at an effective amount, as defined herein above. Optionally however, the preservative can be used at a level which provides an antimicrobial effect on the treated fabrics. Even when the preservative is used in this capacity, it is preferable that an effective level of cyclodextrin molecules remain uncomplexed in the solution in order to provide the odor absorbing benefit.

(C) PERFUME

The odor absorbing composition of the present invention can also optionally provide a "scent signal" in the form of a pleasant odor which signals the removal of malodor from fabrics. The scent signal is designed to provide a fleeting perfume scent, and is not designed to be overwhelming or to be used as an odor masking ingredient. When perfume is added as a scent signal, it is added only at very low levels, e.g., from about 0% to about 0.5%, preferably from about 0.003% to about 0.3%, more preferably from about 0.005% to about 0.2%, by weight of the composition.

Perfume can also be added as a more intense odor in product and on surfaces. When stronger levels of perfume are preferred, relatively higher levels of perfume can be added. It is essential, however, that the perfume be added at a level wherein even if all of the perfume in the composition were to complex with the cyclodextrin molecules, there will still be an effective level of uncomplexed cyclodextrin molecules present in the solution to provide adequate odor control. In order to reserve an effective amount of cyclodextrin molecules for odor control, perfume is typically present at a level wherein less than about 90% of the cyclodextrin complexes with the perfume, preferably less than about 50% of the cyclodextrin complexes with the perfume, more preferably, less than about 30% of the cyclodextrin complexes with the perfume, and most preferably, less than about 10% of the cyclodextrin complexes with the perfume. The cyclodextrin to perfume weight ratio should be greater than about 8:1, preferably greater than about 10:1, more preferably greater than about 20:1, even more preferably greater than 40:1 and most preferably greater than about 70:1.

Any type of perfume can be incorporated into the composition of the present invention. There are however, perfume characteristics which are preferred for use on fabrics in order to provide a fresh fabric impression and perfume characteristics which are preferred for household use.

Preferably, at least about 25%, more preferably at least about 50%, most preferably at least about 75%, by weight of the perfume is composed of fragrance material selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones havingmolecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and essentially free from nitromusks and halogenated fragrance materials.

More preferably, at least about 25%, more preferably at least about 50%, most preferably at least about 75%, by weight of the perfume is composed of fragrance material selected from the group consisting of:

| Common Name | Chemical Type | Chemical Name | Approx. M.W. |
|---|---|---|---|
| adoxal | aliphatic aldehyde | 2,6,10-trimethyl-9-undecen-1-al | 210 |
| allyl amyl glycolate | ester | allyl amyl glycolate | 182 |
| allyl cyclohexane propionate | ester | allyl-3-cyclohexyl propionate | 196 |
| amyl acetate | ester | 3-methyl-1-butanol acetate | 130 |
| amyl salicylate | ester | amyl salicylate | 208 |
| anisic aldehyde | aromatic aldehyde | 4-methoxy benzaldehyde | 136 |
| aurantiol | schiff base | condensation product of methyl anthranilate and hydroxycitronellal | 305 |
| bacdanol | aliphatic alcohol | 2-ethyl-4-(2,2,3-trimethyl-3-cyclopenten-1-yl)-2-buten-1-ol | 208 |
| benzaldehyde | aromatic aldehyde | benzaldehyde | 106 |
| benzophenone | aromatic ketone | benzophenone | 182 |
| benzyl acetate | ester | benzyl acetate | 150 |
| benzyl salicylate | ester | benzyl salicylate | 228 |
| beta damascone | aliphatic ketone | 1-(2,6,6-trimethyl-1-cyclo-hexen-1-yl)-2-buten-1-one | 192 |
| beta gamma hexanol | alcohol | 3-hexen-1-ol | 100 |
| buccoxime | aliphatic ketone | 1,5-dimethyl-oxime bicyclo[3,2,1]octan-8-one | 167 |
| cedrol | alcohol | octahydro-3,6,8,8-tetramethyl-1H-3A,7-methanoazulen-6-ol | 222 |
| cetalox | ether | dodecahydro-3A,6,6,9A-tetramethylnaphtho[2,1B]-furan | 236 |
| cis-3-hexenyl acetate | ester | cis-3-hexenyl acetate | 142 |
| cis-3-hexenyl salicylate | ester | beta, gamma-hexenyl salicylate | 220 |
| citronellol | alcohol | 3,7-dimethyl-6-octenol | 156 |
| citronellyl nitrile | nitrile | geranyl nitrile | 151 |
| clove stem oil | natural | | |
| coumarin | lactone | coumarin | 146 |
| cyclohexyl salicylate | ester | cyclohexyl salicylate | 220 |
| cymal | aromatic aldehyde | 2-methyl-3-(para iso | 190 |

| Common Name | Chemical Type | Chemical Name | Approx. M.W. |
|---|---|---|---|
| decyl aldehyde | aliphatic aldehyde | propyl phenyl) propionaldehyde decyl aldehyde | 156 |
| delta damascone | aliphatic ketone | 1-(2,6,6-trimethyl-3-cyclo-hexen-1-yl)-2-buten-1-one | 192 |
| dihydromyrcenol | alcohol | 3-methylene-7-methyl octan-7-ol | 156 |
| dimethyl benzyl carbinyl acetate | ester | dimethyl benzyl carbinyl acetate | 192 |
| ethyl vanillin | aromatic aldehyde | ethyl vanillin | 166 |
| ethyl-2-methyl butyrate | ester | ethyl-2-methyl butyrate | 130 |
| ethylene brassylate | macrocyclic lactone | ethylene tridecan-1,13-dioate | 270 |
| eucalyptol | aliphatic epoxide | 1,8-epoxy-para-menthane | 154 |
| eugenol | alcohol | 4-allyl-2-methoxy phenol | 164 |
| exaltolide | macrocyclic lactone | cyclopentadecanolide | 240 |
| flor acetate | ester | dihydro-nor-cyclopentadienyl acetate | 190 |
| florhydral | aromatic aldehyde | 3-(3-isopropylphenyl) butanal | 190 |
| frutene | ester | dihydro-nor-cyclopentadienyl propionate | 206 |
| galaxolide | ether | 1,3,4,6,7,8-hexahydro-4,6,6,7,8,8-hexamethylcyclopenta-gamma-2-benzopyrane | 258 |
| gamma decalactone | lactone | 4-N-hepty-4-hydroxybutanoic acid lactone | 170 |
| gamma dodecalactone | lactone | 4-N-octyl-4-hydroxy-butanoic acid lactone | 198 |
| geraniol | alcohol | 3,7-dimethyl-2,6-octadien-1-ol | 154 |
| geranyl acetate | ester | 3,7-dimethyl-2,6-octadien-1-yl acetate | 196 |
| geranyl nitrile | ester | 3,7-dimethyl-2,6-octadienenitrile | 149 |
| helional | aromatic aldehyde | alpha-methyl-3,4,(methylenedioxy) hydrocinnamaldehyde | 192 |
| heliotropin | aromatic aldehyde | heliotropin | 150 |
| hexyl acetate | ester | hexyl acetate | 144 |
| hexyl cinnamic aldehyde | aromatic aldehyde | alpha-n-hexyl cinnamic aldehyde | 216 |
| hexyl salicylate | ester | hexyl salicylate | 222 |
| hydroxyambran | aliphatic alcohol | 2-cyclododecyl-propanol | 226 |
| hydroxycitronellal | aliphatic aldehyde | hydroxycitronellal | 172 |
| ionone alpha | aliphatic ketone | 4-(2,6,6-trimethyl-1-cyclohexenyl-1-yl)-3-buten-2-one | 192 |
| ionone beta | aliphatic ketone | 4-(2,6,6-trimethyl-1-cyclohexen-1-yl)-3-butene-2-one | 192 |
| ionone gamma methyl | aliphatic ketone | 4-(2,6,6-trimethyl-2-cyclohexyl-1-yl)-3-methyl-3-buten-2-one | 206 |
| iso E super | aliphatic ketone | 7-acetyl-1,2,3,4,5,6,7,8-octahydro-1,1,6,7,tetramethyl naphthalene | 234 |
| iso eugenol | ether | 2-methoxy-4-(1-propenyl) phenol | 164 |
| iso jasmone | aliphatic ketone | 2-methyl-3-(2-pentenyl)-2-cyclopenten-1-one | 166 |
| koavone | aliphatic aldehyde | acetyl di-isoamylene | 182 |
| lauric aldehyde | aliphatic aldehyde | lauric aldehyde | 184 |
| lavandin | natural | | |
| lavender | natural | | |
| lemon CP | natural | major component d-limonene | |
| d-limonene/orange terpenes | alkene | 1-methyl-4-iso-propenyl-1-cyclohexene | 136 |
| linalool | alcohol | 3-hydroxy-3,7-dimethyl-1,6-octadiene | 154 |
| linalyl acetate | ester | 3-hydroxy-3,7-dimethyl-1,6-octadiene acetate | 196 |
| lrg 201 | ester | 2,4-dihydroxy-3,6-dimethyl benzoic acid methyl ester | 196 |
| lyral | aliphatic aldehyde | 4-(4-hydroxy-4-methyl-pentyl) 3-cyclohexene-1-carboxaldehyde | 210 |
| majantol | aliphatic alcohol | 2,2-dimethyl-3-(3-methylphenyl)-propanol | 178 |
| mayol | alcohol | 4-(1-methylethyl) cyclohexane methanol | 156 |
| methyl anthranilate | aromatic amine | methyl-2-aminobenzoate | 151 |
| methyl beta naphthyl ketone | aromatic ketone | methyl beta naphthyl ketone | 170 |
| methyl cedrylone | aliphatic ketone | methyl cedrenyl ketone | 246 |
| methyl chavicol | ester | 1-methyloxy-4,2-propen-1-yl benzene | 148 |
| methyl dihydro jasmonate | aliphatic ketone | methyl dihydro jasmonate | 226 |
| methyl nonyl acetaldehyde | aliphatic aldehyde | methyl nonyl acetaldehyde | 184 |
| musk indanone | aromatic ketone | 4-acetyl-6-tert butyl-1,1-dimethyl indane | 244 |
| nerol | alcohol | 2-cis-3,7-dimethyl-2,6-octadien-1-ol | 154 |
| nonalactone | lactone | 4-hydroxynonanoic acid, lactone | 156 |
| norlimbanol | aliphatic alcohol | 1-(2,2,6-trimethyl-cyclohexyl)-3-hexanol | 226 |
| orange CP | natural | major component d-limonene | |
| P. T. bucinal | aromatic aldehyde | 2-methyl-3(para tert butylphenyl) propionaldehyde | 204 |
| para hydroxy phenyl butanone | aromatic ketone | para hydroxy phenyl butanone | 164 |
| patchouli | natural | | |
| phenyl acetaldehyde | aromatic aldehyde | 1-oxo-2-phenylethane | 120 |
| phenyl acetaldehyde dimethyl acetal | aromatic aldehyde | phenyl acetaldehyde dimethyl acetal | 166 |
| phenyl ethyl acetate | ester | phenyl ethyl acetate | 164 |
| phenyl ethyl alcohol | alcohol | phenyl ethyl alcohol | 122 |
| phenyl ethyl phenyl acetate | ester | 2-phenylethyl phenyl acetate | 240 |
| phenyl hexanol/ phenoxanol | alcohol | 3-methyl-5-phenylpentanol | 178 |
| polysantol | aliphatic alcohol | 3,3-dimethyl-5-(2,2,3-trimethyl-3-cyclopenten-1-yl)-4-penten-2-ol | 221 |
| prenyl acetate | ester | 2-methylbuten-2-ol-4-acetate | 128 |
| rosaphen | aromatic alcohol | 2-methyl-5-phenyl pentanol | 178 |
| sandalwood | natural | | |
| alpha-terpinene | aliphatic alkane | 1-methyl-4-iso-propylcyclohexadiene-1,3 | 136 |
| terpineol (alpha terpineol and beta terpineol) | alcohol | para-menth-1-en-8-ol, para-menth-1-en-1-ol | 154 |
| terpinyl acetate | ester | para-menth-1-en-8-yl acetate | 196 |
| tetra hydro linalool | aliphtic alcohol | 3,7-dimethyl-3-octanol | 158 |

-continued

| Common Name | Chemical Type | Chemical Name | Approx. M.W. |
|---|---|---|---|
| tetrahydromyrcenol | aliphatic alcohol | 2,6-dimethyl-2-octanol | 158 |
| tonalid/musk plus | aromatic ketone | 7-acetyl-1,1,3,4,4,6-hexamethyl tetralin | 258 |
| undecalactone | lactone | 4-N-heptyl-4-hydroxybutanoic acid lactone | 184 |
| undecavertol | alcohol | 4-methyl-3-decen-5-ol | 170 |
| undecyl aldehyde | aliphatic aldehyde | undecanal | 170 |
| undecylenic aldehyde | aliphatic aldehyde | undecylenic aldehyde | 168 |
| vanillin | aromatic aldehyde | 4-hydroxy-3-methoxybenzaldehyde | 152 |
| verdox | ester | 2-tert-butyl cyclohexyl acetate | 198 |
| vertenex | ester | 4-tert-butyl cyclohexyl acetate | 198 | and mixtures thereof.

When high initial perfume odor impact on fabrics is desired, it is also preferable to select a perfume containing perfume ingredients which are not too hydrophobic. The less hydrophobic perfume ingredients are more soluble in water, and are more available in the odor absorbing composition. The degree of hydrophobicity of a perfume ingredient can be correlated with its octanol/water partitioning coefficient P. The octanol/water partitioning coefficient of a perfume ingredient is the ratio between its equilibrium concentration in octanol and in water. A perfume ingredient with a greater partitioning coefficient P is more hydrophobic. Conversely, a perfume ingredient with a smaller partitioning coefficient P is more hydrophilic. The preferred perfume ingredients of this invention have an octanol/water partitioning coefficient P of about 1,000 or smaller. Since the partitioning coefficients of the perfume ingredients normally have high values, they are more conveniently given in the form of their logarithm to the base 10, logP. Thus the perfume ingredients of this invention have logP of about 3 or smaller.

The logP of many perfume ingredients has been reported; for example, the Pomona 92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona 92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of perfume ingredients which have ClogP values of about 3 or smaller are benzaldehyde, benzyl acetate, cis-3-hexenyl acetate, coumarin, dihydromyrcenol, dimethyl benzyl carbinyl acetate, ethyl vanillin, eucalyptol, eugenol, iso eugenol, flor acetate, geraniol, hydroxycitronellal, koavone, linalool, methyl anthranilate, methyl beta naphthyl ketone, methyl dihydro jasmonate, nerol, nonalactone, phenyl ethyl acetate, phenyl ethyl alcohol, alpha terpineol, beta terpineol, vanillin, and mixtures thereof.

When hydrophilic perfume is desired, at least about 25% by weight of the perfume, more preferably about 50%, most preferably about 75%, is composed of perfume ingredients having a ClogP of about 3 or smaller.

Cyclodextrin molecules are known for their ability to form complexes with perfume ingredients and have typically been taught as a perfume carrier. The prior art teaches the use of drier-added fabric softener sheets containing high levels of cyclodextrin/perfume complexes wherein the fabrics treated with this solid cyclodextrin complex release perfume when the fabrics are rewetted. The art also teaches that cyclodextrin/perfume complexes used in aqueous rinse-added fabric softener compositions must be protected with a hydrophobic wax coating so the cyclodextrin/perfume complexes will not decompose due to the presence of water. See U.S. Pat. No. 5,102,564 Gardlik et al., issued Apr. 7, 1992; U.S. Pat. No. 5,234,610 Gardlik et al., issued Aug. 10, 1993; U.S. Pat. No. 5,234,611 Trinh, et al., issued Aug. 10, 1993. It is therefore highly surprising and unexpected to find that fabrics treated with the aqueous compositions of the present invention, which contain low levels of uncomplexed cyclodextrin and even lower levels of perfume, also exhibit perfume release upon rewetting. This phenomenon creates a benefit in that fabrics treated with the composition of the present invention will thus remain fresh longer, via a perfume release, when said fabrics are rewetted, such as when the wearer perspires.

(D) CARRIER

Aqueous solutions are preferred for odor control. The dilute aqueous solution provides the maximum separation of cyclodextrin molecules on the fabric and thereby maximizes the chance that an odor molecule will interact with a cyclodextrin molecule.

The preferred carrier of the present invention is water. The water which is used can be distilled, deionized, or tap water. Water not only serves as the liquid carrier for the cyclodextrins, but it also facilitates the complexation reaction between the cyclodextrin molecules and any malodorous molecules that are on the fabric when it is treated. It has recently been discovered that water has an unexpected odor controlling effect of its own. It has been discovered that the intensity of the odor generated by some polar, low molecular weight organic amines, acids, and mercaptans is reduced when the odor-contaminated fabrics are treated with an aqueous solution. Not to be bound by theory, it is believed that water solubilizes and depresses the vapor pressure of these polar, low molecular weight organic molecules, thus reducing their odor intensity.

(E) OPTIONAL INGREDIENTS

The composition of the present invention can optionally contain adjunct odor-controlling materials, chelating agents, solubilizing aids, antifoaming agents, defoaming agents, antistatic agents, insect and moth repelling agents, colorants, especially bluing agents, antioxidants, and mixtures thereof. Incorporating adjunct odor-controlling materials can enhance the capacity of the cyclodextrin to control odors as well as broaden the range of odor types and molecule sizes which can be controlled. Such materials include, for example, metallic salts, water-soluble cationic and anionic polymers, water-soluble bicarbonate salts, zeolites, activated carbon, and mixtures thereof.

(1) Metallic Salt

Optionally, but highly preferred, the present invention can include metallic salts for added odor absorption and/or antimicrobial benefit for the cyclodextrin solution. The metallic salts are selected from the group consisting of copper salts, zinc salts, and mixtures thereof.

Copper salts have some antimicrobial benefits. Specifically, cupric abietate acts as a fungicide, copper acetate acts as a mildew inhibitor, cupric chloride acts as a fungicide, copper lactate acts as a fungicide, and copper sulfate acts as a germicide. Copper salts also possess some malodor control abilities. See U.S. Pat. No. 3,172,817, Leupold, et al., which discloses deodorizing compositions for treating disposable articles, comprising at least slightly water-soluble salts of acylacetone, including copper salts and zinc salts; said patents are incorporated herein by reference.

The preferred salts possess malodor control abilities. Zinc has been used most often for its ability to ameliorate malodor, e.g., in mouth wash products, as disclosed in U.S. Pat. No. 4,325,939, issued Apr. 20, 1982 and U.S. Pat. No. 4,469,674, issued Sept. 4, 1983, to N. B. Shah, et al., all of which are incorporated herein by reference. Highly-ionized and soluble zinc salts such as zinc chloride, provide the best source of zinc ions. Zinc borate functions as a fungistat and a mildew inhibitor, zinc caprylate functions as a fungicide, zinc chloride provides antiseptic and deodorant benefits, zinc ricinoleate functions as a fungicide, zinc sulfate heptahydrate functions as a fungicide and zinc undecylenate functions as a fungistat.

Preferably the metallic salts are water-soluble zinc salts, copper salts or mixtures thereof, and more preferably zinc salts, especially $ZnCl_2$. These salts are preferably present in the present invention primarily to absorb amine and sulfur-containing compounds that have molecular sizes too small to be effectively complexed with the cyclodextrin molecules. Low molecular weight sulfur-containing materials, e.g., sulfide and mercaptans, are components of many types of malodors, e.g., food odors (garlic, onion), body/perspiration odor, breath odor, etc. Low molecular weight amines are also components of many malodors, e.g., food odors, body odors, urine, etc.

When metallic salts are added to the composition of the present invention they are typically present at a level of from about 0.1% to about 10%, preferably from about 0.2% to about 7%, more preferably from about 0.3% to about 5% by weight of the composition. When zinc salts are used as the metallic salt, and a clear solution is desired, it is preferable that the pH of the solution is adjusted to less than about 7, more preferably less than about 6, most preferably less than about 5, in order to keep the solution clear.

(2) Water-Soluble Polymers

Some water-soluble polymers, e.g., water-soluble cationic polymer and water-soluble anionic polymers can be used in the composition of the present invention to provide additional odor control benefits.

(a) Cationic polymers, e.g., polyamines

Water-soluble cationic polymers, e.g., those containing amino functionalities, amido functionalities, and mixtures thereof, are useful in the present invention to control certain acid-type odors.

(b) Anionic polymers, e.g., polyacrylic acid

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280® from Calgon.

(3) Low Molecular Weight Polyols

Low molecular weight polyols with relatively high boiling points, as compared to water, such as ethylene glycol, propylene glycol and/or glycerol are preferred optional ingredients for improving odor control performance of the composition of the present invention. Not to be bound by theory, it is believed that the incorporation of a small amount of low molecular weight glycols into the composition of the present invention enhances the formation of the cyclodextrin inclusion complexes as the fabric dries.

It is believed that the polyols' ability to remain on the fabric for a longer period of time than water, as the fabric dries, allows them to form ternary complexes with the cyclodextrin and some malodorous molecules. The addition of the glycols is believed to fill up void space in the cyclodextrin cavity that is unable to be filled by some malodor molecules of relatively smaller sizes. Preferably the glycol used is ethylene glycol, and/or propylene glycol. Cyclodextrins prepared by processes that result in a level of such polyols are highly desirable, since they can be used without removal of the polyols.

When glycols are added to the composition of the present invention the preferred weight ratio of low molecular weight polyol to cyclodextrin is from about 1:1,000 to about 20:100, more preferably from about 3:1,000 to about 15:100, even more preferably from about 5:1,000 to about 10:100, and most preferably from about 1:100 to about 7:100.

(4) Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention it is preferably that incompatible metal salts not be present in the invention. Preferably, when these salts are used the composition should be essentially free of zinc and other incompatible metal ions, e.g., Ca, Fe, Ba, etc., which form water-insoluble salts.

(5) Chelating Agents

Some amine/acid chelating agents such as ethylenediaminetetraacetic acid (EDTA) can optionally be added to the composition of the present invention in order to enhance the activity of the water-soluble, antimicrobial preservative. When a chelating agent is added to the composition of the present invention, it is typically present at a level of from about 0.01% to about 0.3%, preferably from about 0.05% to about 0.2%. It is important that the composition of the present invention be essentially free of any added metal ions that can be chelated by any chelating agent that is added to the composition of the present invention because such metal ions complex with, and deactivate, the chelating agents.

(6) Antistatic Agents

The composition of the present invention can optionally contain an effective amount of antistatic agent to provide the treated clothes with in-wear static. Preferred antistatic agents are those that are water soluble in at least effective amount, such that the composition remains a clear solution. Examples of these antistatic agents are monoalkyl cationic quaternary ammonium compounds, e.g., mono($C_{10}$–$C_{14}$ alkyl)trimethyl ammonium halide, such as monolauryl trimethyl ammonium chloride, hydroxycetyl hydroxyethyl dimethyl ammonium chloride, available under the trade name Dehyquart E® from Henkel, and ethyl bis(polyethoxy ethanol)alkylammonium ethylsulfate, available under the trade name Variquat 66® from Witco Corp., polyethylene glycols, polymeric quaternary ammonium salts, such as polymers conforming to the general formula:

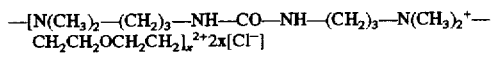

available under the trade name Mirapol A-15® from Rhône-Poulenc, and

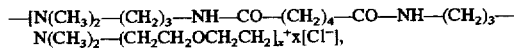

available under the trade name Mirapol AD-1® from Rhône-Poulenc, quaternized polyethyleneimines, vinylpyrrolidone/methacrylamidopropyltrimethylammonium chloride copolymer, available under the trade name Gafquat HS-100® from GAF; triethonium hydrolyzed collagen ethosulfate, available under the trade name Quat-Pro E® from Maybrook; and mixtures thereof.

It is preferred that a no foaming, or low foaming, agent is used, to avoid foam formation during fabric treatment. It is also preferred that polyethoxylated agents such as polyethylene glycol or Variquat 66® are not used when alpha-cyclodextrin is used. The polyethoxylate groups have a strong affinity to, and readily complex with, alpha-cyclodextrin which in turn depletes the uncomplexed cyclodextrin available for odor control.

When an antistatic agent is used it is typically present at a level of from about 0.05% to about 10%, preferably from about 0.1% to about 5%, more preferably from about 0.3% to about 3%, by weight of the composition.

(7) Insect and/or Moth Repelling Agent

The composition of the present invention can optionally contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citranellal, citral, linalool, cedar extract, geranium oil, sandalwood oil, 2-(diethylphenoxy)ethanol, etc. Other examples of insect and/or moth repellents useful in the composition of the present invention are disclosed in U.S. Pat. Nos. 4,449,987, 4,693,890, 4,696,676, 4,933,371, 5,196,200, and in "Semio Activity of Flavor and Fragrance Molecules on Various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35–48, all of said patents and publications being incorporated herein by reference. When an insect and/or moth repellent is used it is typically present at a level of from about 0.005% to about 3%, by weight of the composition.

(8) Solubilizing Aid

The odor absorbing composition of the present invention can also optionally contain a solubilizing aid to solubilize any excess hydrophobic organic materials, e.g., perfume, insect repelling agent, antioxidant, etc., that are not readily soluble in the composition, to form a clear solution. A suitable solubilizing aid is surfactant, preferably no-foaming or low-foaming surfactant. Suitable surfactants are nonionic surfactants, anionic surfactants, cationic surfactants, amphoteric surfactants, zwitterionic surfactants, and mixtures thereof. Suitable surfactants can be emulsifiers and/or detersive surfactants. Mixtures of emulsifiers and detersive surfactants are also preferred. When a surfactant containing one, or more, aliphatic alkyl group is used, it is preferred that it contain relatively short alkyl chains of from about 5 to about 14 carbon atoms. Preferred nonionic surfactants are polyethylene glycol-polypropylene glycol block copolymers, such as Puronic® and Pluronic R® surfactants from BASF; Tetronic® and Tetronic R® surfactants from BASF, ethoxylated branched aliphatic diols such as Surfynol® surfactants from Air Products; ethoxylated alkyl phenols, such as Igepal® surfactants from Rhône-Poulenc; ethoxylated aliphatic alcohols and carboxylic acids; polyethylene glycol diesters of fatty acids; fatty acid esters of ethoxylated sorbitans; and mixtures thereof. Preferred anionic surfactants are dialkyl sulfosuccinate, alkylarylsulfonate, fatty alcohol sulfate, paraffin sulfonate, alkyl sarcosinate, alkyl isethionate salts having suitable cations, e.g., sodium, potassium, alkanol ammonium, etc., and mixtures thereof. Preferred amphoteric surfactants are the betaines. It is preferred that the surfactant have good wetting properties. Also preferred are surfactants that have the hydrophilic groups situated between hydrophobic chains, such as Pluronic R® surfactants, Surfynol surfactants, polyethylene glycol diesters of fatty acids, fatty acid esters of ethoxylated sorbitans, dialkyl sulfosuccinate, di($C_8$–$C_{12}$ alkyl)di(C1–C2 alkyl)ammonium halides, and mixtures thereof; or surfactants that have the hydrophobic chains situated between hydrophilic groups, such as Pluronic surfactants; and mixtures thereof. Mixtures of these surfactants and other types of surfactants are also preferred to form no-foaming or low-foaming solubilizing agents. Polyalkylene glycol can be used as a defoaming agent in combination with the solubilizing agents.

If solubilizing agent is used in the present compositions, it is typically used at a level of from about 0.05% to about 1% by weight of the composition, more preferably from about 0.05% to about 0.3%.

(9) Additional Odor Absorbers

When the clarity of the solution is not needed, and the solution is not sprayed on fabrics, other optional odor absorbing materials, e.g., zeolites and/or activated carbon, can also be used.

(a) Zeolites

A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. These materials are typically available as a white powder in the 3–5 micron particle size range. Such materials are preferred over the intermediate zeolites for control of sulfur-containing odors, e.g., thiols, mercaptans.

(b) Activated Carbon

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

It is preferred that no, or essentially no, volatile low molecular weight monohydric alcohols such as ethanol and/or isopropanol are intentionally added to the composition of the present invention since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, it is preferable that the level of monohydric alcohol be less than about 5%, preferably less than about 3%, more preferably less than about 1%.

(10) Colorant

Colorants and dyes, especially bluing agents, can be optionally added to the odor absorbing compositions for visual appeal and performance impression. When colorants are used, they are used at extremely low levels to avoid fabric staining. Preferred colorants for use in the present compositions are highly water-soluble dyes, e.g., Liquitint® dyes available from Milliken Chemical Co. Non-limiting examples of suitable dyes are, Liquitint Blue HP®, Liquitint Blue 65®, Liquitint Patent Blue®, Liquitint Royal Blue®, Liquitint Experimental Yellow 8949-43®, Liquitint Green HMC®, Liquitint Yellow II®, and mixtures thereof, preferably Liquitint Blue HP®, Liquitint Blue 65®, Liquitint Patent Blue®, Liquitint Royal Blue®, Liquitint Experimental Yellow 8949-43®, and mixtures thereof.

II. ARTICLE OF MANUFACTURE

The composition of the present invention can also be used in an article of manufacture comprising said composition plus a spray dispenser. When the commercial embodiment of the article of manufacture is used, it is optional, but preferable, to include the preservative. Therefore, the most basic article of manufacture comprises uncomplexed cyclodextrin, a carrier, and a spray dispenser.

SPRAY DISPENSER

The article of manufacture herein comprises a spray dispenser. The cyclodextrin composition is placed into a spray dispenser in order to be distributed onto the fabric. Said spray dispenser is any of the manually activated means for producing a spray of liquid droplets as is known in the art, e.g. trigger-type, pump-type, non-aerosol self-pressurized, and aerosol-type spray means. The spray dispenser herein does not include those that will substantially foam the clear, aqueous odor absorbing composition. It is preferred that at least about 80%, more preferably, at least about 90% of the droplets have a particle size of larger than about 30 μm The spray dispenser can be an aerosol dispenser. Said aerosol dispenser comprises a container which can be constructed of any of the conventional materials employed in fabricating aerosol containers. The dispenser must be capable of withstanding internal pressure in the range of from about 20 to about 110 p.s.i.g., more preferably from about 20 to about 70 p.s.i.g. The one important requirement concerning the dispenser is that it be provided with a valve member which will permit the clear, aqueous odor absorbing composition contained in the dispenser to be dispensed in the form of a spray of very fine, or finely divided, particles or droplets. The aerosol dispenser utilizes a pressurized sealed container from which the clear, aqueous odor-absorbing composition is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, are not preferred. Halogenated hydrocarbon propellants such as chlorofluoro hydrocarbons have been alleged to contribute to environmental problems. Hydrocarbon propellants can form complexes with the cyclodextrin molecules thereby reducing the availability of uncomplexed cyclodextrin molecules for odor absorption. Preferred propellants are compressed air, nitrogen, inert gases, carbon dioxide, etc. A more complete description of commercially available aerosol-spray dispensers appears in U.S. Pat. No. : 3,436,772, Stebbins, issued Apr. 8, 1969; and U.S. Pat. No. 3,600,325, Kaufman et al., issued Aug. 17, 1971; both of said references are incorporated herein by reference.

Preferably the spray dispenser can be a self-pressurized non-aerosol container having a convoluted liner and an elastomeric sleeve. Said self-pressurized dispenser comprises a liner/sleeve assembly containing a thin, flexible radially expandable convoluted plastic liner of from about 0.010 to about 0.020 inch thick, inside an essentially cylindrical elastomeric sleeve. The liner/sleeve is capable of holding a substantial quantity of odor-absorbing fluid product and of causing said product to be dispensed. A more complete description of self-pressurized spray dispensers can be found in U.S. Pat. No. 5,111,971, Winer issued May 12, 1992, and U.S. Pat. No. 5,232,126, Winer, issued Aug. 3, 1993; both of said references are herein incorporated by reference. Another type of aerosol spray dispenser is one wherein a barrier separates the odor absorbing composition from the propellant (preferably compressed air or nitrogen), as is disclosed in U.S. Pat. No. 4,260,110, issued Apr. 7, 1981, incorporated herein by reference. Such a dispenser is available from EP Spray Systems, East Hanover, N.J.

More preferably, the spray dispenser is a non-aerosol, manually activated, pump-spray dispenser. Said pump-spray dispenser comprises a container and a pump mechanism which securely screws or snaps onto the container. The container comprises a vessel for containing the aqueous odor-absorbing composition to be dispensed.

The pump mechanism comprises a pump chamber of substantially fixed volume, having an opening at the inner end thereof. Within the pump chamber is located a pump stem having a piston on the end thereof disposed for reciprocal motion in the pump chamber. The pump stem has a passageway there through with a dispensing outlet at the outer end of the passageway and an axial inlet port located inwardly thereof.

The container and the pump mechanism can be constructed of any conventional material employed in fabricating pump-spray dispensers, including, but not limited to:

polyethylene; polypropylene; polyethyleneterephthalate; blends of polyethylene, vinyl acetate, and rubber elastomer. A preferred container is made of clear, e.g., polyethylene terephthalate. Other materials can include stainless steel. A more complete disclosure of commercially available dispensing devices appears in: U.S. Pat. No.: 4,895,279, Schultz, issued Jan. 23, 1990; U.S. Pat. No. 4,735,347, Schultz et al., issued Apr. 5, 1988; and U.S. Pat. No. 4,274,560, Carter, issued Jun. 23, 1981; all of said references are herein incorporated by reference.

Most preferably, the spray dispenser is a manually activated trigger-spray dispenser. Said trigger-spray dispenser comprises a container and a trigger both of which can be constructed of any of the conventional material employed in fabricating trigger-spray dispensers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear, e.g. polyethylene terephthalate. The trigger-spray dispenser does not incorporate a propellant gas into the odor-absorbing composition, and preferably it does not include those that will foam the odor-absorbing composition. The trigger-spray dispenser herein is typically one which acts upon a discrete amount of the odor-absorbing composition itself, typically by means of a piston or a collapsing bellows that displaces the composition through a nozzle to create a spray of thin liquid. Said trigger-spray dispenser typically comprises a pump chamber having either a piston or bellows which is movable through a limited stroke response to the trigger for varying the volume of said pump chamber. This pump chamber or bellows chamber collects and holds the product for dispensing. The trigger spray dispenser typically has an outlet check valve for blocking communication and flow of fluid through the nozzle and is responsive to the pressure inside the chamber. For the piston type trigger sprayers, as the trigger is compressed, it acts on the fluid in the chamber and the spring, increasing the pressure on the fluid. For the bellows spray dispenser, as the bellows is compressed, the pressure increases on the fluid. The increase in fluid pressure in either trigger spray dispenser acts to open the top outlet check valve. The top valve allows the product to be forced through the swirl chamber and out the nozzle to form a discharge pattern. An adjustable nozzle cap can be used to vary the pattern of the fluid dispensed.

For the piston spray dispenser, as the trigger is released, the spring acts on the piston to return it to its original position. For the bellows spray dispenser, the bellows acts as the spring to return to its original position. This action causes a vacuum in the chamber. The responding fluid acts to close the outlet valve while opening the inlet valve drawing product up to the chamber from the reservoir.

A more complete disclosure of commercially available dispensing devices appears in U.S. Pat. No. 4,082,223, Nozawa, issued Apr. 4, 1978; U.S. Pat. No. 4,161,288, McKinney, issued Jul. 17, 1985; U.S. Pat. No. 4,434,917, Saito et al., issued Mar. 6, 1984; and U.S. Pat. No. 4,819,835, Tasaki, issued Apr. 11, 1989; U.S. Pat. No. 5,303,867, Peterson, issued Apr. 19, 1994; all of said references are incorporated herein by reference.

A broad array of trigger sprayers or finger pump sprayers are suitable for use with the compositions of this invention. These are readily available from suppliers such as Calmar, Inc., City of Industry, Calif.; CSI (Continental Sprayers, Inc.), St. Peters, Mo.; Berry Plastics Corp., Evansville, Id.—a distributor of Guala® sprayers; or Seaquest Dispensing, Cary, Ill.

The preferred trigger sprayers are the blue inserted Guala® sprayer, available from Berry Plastics Corp., or the Calmar TS800-1A sprayers, available from Calmar Inc., because of the fine uniform spray characteristics, spray volume, and pattern size. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or clear polyethylene terephthalate.

For smaller four fl-oz. size (about 118 ml), a finger pump can be used with canister or cylindrical bottle. The preferred pump for this application is the cylindrical Euromist II® from Seaquest Dispensing.

III. METHOD OF USE

The cyclodextrin solution herein can be used by distributing, e.g., by placing the aqueous solution into a dispensing means, preferably a spray dispenser and spraying an effective amount onto the desired surface or article. An effective amount as defined herein means an amount sufficient to absorb odor to the point that it is not discernible by the human sense of smell yet not so much as to saturate or create a pool of liquid on said article or surface and so that when dry there is no visual deposit readily discernible. Distribution can be achieved by using a spray device, a roller, a pad, etc.

Preferably, the present invention does not encompass distributing the cyclodextrin solution on to shiny surfaces including, e.g., chrome, glass, smooth vinyl, leather, shiny plastic, shiny wood, etc. It is preferable not to distribute the cyclodextrin solution onto shiny surfaces because spotting and filming can more readily occur on the surfaces. Furthermore, the cyclodextrin solution is not for use on human skin, especially when an antimicrobial preservative is present in the composition because skin irritation can occur.

The present invention encompasses the method of spraying an effective amount of cyclodextrin solution onto household surfaces. Preferably said household surfaces are selected from the group consisting of countertops, cabinets, walls, floors, bathroom surfaces and kitchen surfaces.

The present invention encompasses the method of spraying a mist of an effective amount of cyclodextrin solution onto fabric and/or fabric articles. Preferably, said fabric and/or fabric articles include, but are not limited to, clothes, curtains, drapes, upholstered furniture, carpeting, bed linens, bath linens, tablecloths, sleeping bags, tents, car interior, e.g., car carpet, fabric car seats, etc.

The present invention encompasses the method of spraying a mist of an effective amount of cyclodextrin solution onto and into shoes wherein said shoes are not sprayed to saturation.

The present invention encompasses the method of spraying a mist of an effective amount of cyclodextrin solution onto shower curtains.

The present invention relates to the method of spraying a mist of an effective amount of cyclodextrin solution onto and/or into garbage cans and/or recycling bins.

The present invention relates to the method of spraying a mist of an effective amount of cyclodextrin solution into the air to absorb malodor.

The present invention relates to the method of spraying a mist of an effective amount of cyclodextrin solution into and/or onto major household appliances including but not limited to: refrigerators, freezers, washing machines, automatic dryers, ovens, microwave ovens, dishwashers etc., to absorb malodor.

The present invention relates to the method of spraying a mist of an effective amount of cyclodextrin solution onto cat litter, pet bedding and pet houses to absorb malodor.

The present invention relates to the method of spraying a mist of an effective amount of cyclodextrin solution onto household pets to absorb malodor.

All percentages, ratios, and parts herein, in the Specification, Examples, and Claims are by weight and are approximations unless otherwise stated.

The following are non-limiting examples of the instant composition. Perfume compositions that are used herein are as follows:

| Perfume Ingredients | A Wt. % | B Wt. % | C Wt. % |
|---|---|---|---|
| 3,7-Dimethyl-6-octenol | 10 | — | 5 |
| Benzyl salicylate | 5 | 20 | 5 |
| Benzyl acetate | 10 | 15 | 5 |
| Benzophenone | 3 | 5 | — |
| Octahydro-3,6,8,8-tetramethyl-1H-3A,7-methanoazulen-6-ol | 2 | — | — |
| 3-Methylene-7-methyl octan-7-ol | 10 | — | 5 |
| Dihydro-nor-cyclopentadienyl acetate | 5 | — | 5 |
| 1,3,4,6,7,8-Hexahydro-4,6,6,7,8,8-hexamethyl-cyclopenta-gamma-2-benzopyrane | 10 | — | — |
| Phenyl ethyl alcohol | 15 | 10 | 20 |
| 3-Hydroxy-3,7-dimethyl-1,6-octadiene acetate | 4 | — | 5 |
| 3-Hydroxy-3,7-dimethyl-1,6-octadiene | 6 | 15 | 5 |
| Methyl dihydro jasmonate | 3 | 10 | 5 |
| 2-Methyl-3(para tert butylphenyl) propionaldehyde | 10 | 15 | 20 |
| Phenyl ethyl acetate | 2 | 5 | 1 |
| 4-Hydroxy-3-methoxybenzaldehyde | — | — | 1 |
| para-Menth-1-en-8-ol, para-menth-1-en-1-ol | 5 | — | 8 |
| Anisic aldehyde | — | — | 2 |
| Coumarin | — | — | 5 |
| 2-Methyl-3-(para iso propylphenyl) propionaldehyde | — | — | 3 |
| Total | 100 | 100 | 100 |

| Perfume Material | D Wt. % | E Wt. % |
|---|---|---|
| Amyl salicylate | 8 | — |
| Benzyl acetate | 8 | 8 |
| Benzyl Salicylate | — | 2 |
| Citronellol | 7 | 27 |
| Dihydromyrcenol | 2 | — |
| Eugenol | 4 | — |
| Flor acetate | 8 | — |
| Galaxolide | 1 | — |
| Geraniol | 5 | — |
| Hexyl cinnamic aldehyde | 2 | — |
| Hydroxycitronellal | 3 | — |
| Lilial | 2 | — |
| Linalool | 12 | 13 |
| Linalyl acetate | 5 | — |
| Lyral | 3 | — |
| Methyl dihydrojasmonate | 3 | — |
| Nerol | 2 | — |
| Phenoxy ethyl propionate | — | 3 |
| Phenylethyl acetate | 5 | 17 |
| Phenylethyl alcohol | 8 | 17 |
| alpha-Terpineol | 5 | 13 |
| alpha-Terpinene | 5 | — |
| Tetrahydromyrcenol | 2 | — |
| Total | 100 | 100 |

Perfume E is composed of about 70%, by weight, of ingredients having ClogP of about 3 or smaller.

The following are non-limiting examples of the instant composition.

| Ingredients | Example I Wt. % | Example II Wt. % |
|---|---|---|
| Methylated beta-cyclodextrin | 1.0 | 0.5 |
| alpha-Cyclodextrin | — | 0.5 |
| Perfume A | 0.01 | 0.01 |
| Kathon CG | 0.001 | 0.0008 |
| Distilled Water | Balance | Balance |

Examples I and II

The ingredients of Examples I and II are mixed and dissolved into clear solutions.

| Ingredients | Example III Wt. % | Example IV Wt. % |
|---|---|---|
| Methylated alpha-cyclodextrin | 0.27 | — |
| Methylated beta-cyclodextrin | 0.73 | 1.0 |
| Perfume A | 0.01 | 0.01 |
| Kathon CG | 0.001 | — |
| Bronopol | — | 0.02 |
| Distilled Water | Balance | Balance |

Example III

The ingredients of Example III are mixed and dissolved into a clear solution. Methylated alpha-cyclodextrin and methylated beta-cyclodextrin are obtained as a mixture from the methylation reaction of a mixture of alpha-cyclodextrin and beta-cyclodextrin.

Example IV

The ingredients of Example IV are mixed and dissolved in a vessel into a clear solution.

| Ingredients | Example V Wt. % | Example VI Wt. % |
|---|---|---|
| alpha-Cyclodextrin | 0.5 | — |
| Hydroxypropyl beta-cyclodextrin | 0.5 | 1.0 |
| Perfume B | 0.01 | 0.01 |
| Kathon CG | 0.0005 | — |
| Sodium Pyrithione | — | 0.001 |
| Distilled water | Balance | Balance |

Examples V and VI

The ingredients of Examples V and VI are mixed and dissolved into clear solutions. The hydroxypropyl-beta-cyclodextrin has a degree of substitution of about 5.0

| Ingredients | Example VII Wt. % | Example VIII Wt. % |
| --- | --- | --- |
| Alpha-cyclodextrin | 0.5 | — |
| Hydroxypropyl alpha-cyclodextrin | — | 0.27 |
| Hydroxypropyl beta-cyclodextrin | 0.5 | 0.73 |
| Propylene glycol | 0.01 | 0.06 |
| Perfume B | — | 0.01 |
| Kathon CG | 0.001 | 0.0008 |
| Distilled water | Balance | Balance |

Example VII

The ingredients of Example VII are mixed and dissolved in a vessel into a clear solution. The hydroxypropyl-beta-cyclodextrin has a degree of substitution of about 5.4.

Example VIII

The ingredients of Example VIII are mixed and dissolved into a clear solution. Hydroxypropyl alpha-cyclodextrin and hydroxypropyl beta-cyclodextrin are obtained as a mixture with an average degree of substitution of about 4.9, from the hydroxypropylation reaction of a mixture of alpha-cyclodextrin and beta-cyclodextrin. Propylene glycol is a minor by-product (about 6%) of the same reaction.

| Ingredients | Example IX Wt. % | Example X Wt. % |
| --- | --- | --- |
| Alpha-cyclodextrin | 0.5 | — |
| Hydroxypropyl alpha-cyclodextrin | — | 1.0 |
| Hydroxypropyl beta-cyclodextrin | 1.0 | 2.5 |
| gamma-Cyclodextrin | 0.5 | 1.0 |
| Perfume C | 0.02 | 0.05 |
| Kathon CG | 0.001 | — |
| Glutaraldehyde | — | 0.01 |
| Ethanol | — | 2.0 |
| Distilled water | Balance | Balance |

Examples IX and X

The ingredients of Examples IX and X are mixed and dissolved into clear solutions.

| Ingredients | Example XI Wt. % | Example XII Wt. % |
| --- | --- | --- |
| Alpha-cyclodextrin | 0.5 | — |
| Methylated beta-cyclodextrin | 0.5 | — |
| Hydroxypropyl alpha-cyclodextrin | — | 0.27 |
| Hydroxypropyl beta-cyclodextrin | — | 0.73 |
| Zinc chloride | 1.0 | 1.0 |
| Perfume D | 0.01 | 0.01 |
| Kathon CG | 0.0008 | 0.0008 |
| Propylene glycol | — | 0.06 |
| HCl | (a) | (a) |
| Distilled water | Balance | Balance |

(a) To adjust solution pH to about 4.8

Example XI

About 5 parts of alpha-cyclodextrin and about 5 parts of methylated beta-cyclodextrin are added with mixing in a vessel containing about 980 parts of distilled water. When the cyclodextrins are totally dissolved into a clear solution, about 10 parts of zinc chloride is added with mixing. Zinc chloride is dissolved into a milky white solution. The solution is adjusted to about pH 4.8 with a very small amount of hydrochloric acid, upon which the solution becomes clear again. About 0.1 part of perfume is added and mixed until the solution is clear. Then about 0.67 part of a nominally 1.5% aqueous solution of Kathon CG is added with mixing until the solution becomes water clear.

Example XII

The composition of Example XII is prepared similarly to that of Example XI.

| Ingredients | Example XIII Wt. % | Example XIV Wt. % |
| --- | --- | --- |
| Alpha-cyclodextrin | 0.5 | 0.5 |
| Methylated beta-cyclodextrin | 1.0 | — |
| Hydroxypropyl beta-cyclodextrin | — | 0.5 |
| Zinc chloride | 1.0 | 1.0 |
| Perfume E | 0.1 | 0.05 |
| Glydant Plus | 0.01 | — |
| Kathon CG | — | 0.0008 |
| HCl | (a) | (a) |
| Distilled water | Balance | Balance |

| Ingredients | Example XV Wt. % | Example XVI Wt % |
| --- | --- | --- |
| Hydroxypropyl alpha-cyclodextrin | 0.27 | 0.27 |
| Hydroxypropyl beta-cyclodextrin | 0.73 | 0.73 |
| Zinc chloride | 1.0 | — |
| ZnSO$_4$.7H$_2$O | — | 2.2 |
| Perfume E | 0.05 | 0.03 |
| Kathon CG | 0.0008 | 0.0008 |
| HCl | (a) | — |
| Distilled water | Balance | Balance |

(a) To adjust solution pH to about 4.8

Examples XIII–XV

The Compositions of Examples XIII–XV are prepared similarly to that of Example XI.

Example XVI

The Composition of Example XVI is prepared similarly to that of Example XV, except that no HCl is needed. The Composition is clear and has a pH of about 6.4.

Example XVII

The Composition of Example VIII is sprayed onto clothing using a blue inserted Guala® trigger sprayer, available from Berry Plastics Corp. and allowed to evaporate off of the clothing.

Example XVIII

The Composition of Example III is sprayed onto a kitchen countertop using blue inserted Guala® trigger sprayer, available from Berry Plastics Corp., and wiped off with a paper towel.

Example XIX

The Composition of Example XIV is sprayed onto clothes using a cylindrical Euromist II® pump sprayer available from Seaquest Dispensing, and allowed to evaporate off of the clothing.

Example XX

The Composition of Example XII is sprayed onto fabric areas, e.g., cloth car seats, carpeting, etc., of a car interior, using a Calmar TS®-800-1A sprayer, and allowed to dry.

What is claimed:

1. A stable, aqueous odor absorbing composition, for use on inanimate surfaces, comprising:
   A. from about 0.1% to about 5%, by weight of the composition, of a solubilized, water-soluble, uncomplexed cyclodextrin;
   B. an effective amount of a solubilized, water-soluble, antimicrobial preservative having a water solubility of greater than about 0.3%;
   C. optional perfume; and
   D. aqueous carrier; and
   wherein said composition is essentially free of any material that would soil or stain fabric and has a pH of greater than about 3, and wherein said composition is either:
   (1) a composition wherein said cyclodextrin is either:
      (a) methylated beta-cyclodextrin or
      (b) a mixture of hydroxypropyl alpha-cyclodextrin and hydroxypropyl beta-cyclodextrin;
   (2) a composition wherein said antimicrobial preservative is selected from the group consisting of:
      (a) an organic sulfur compound selected from the group consisiting of 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; 2-methyl-4-isothiazolin-3-one; 5-chloro-2-methyl-3-isothiazolone; and mixtures thereof; or
      (b) a cyclic organic nitrogen compound selected from the group consisting of imidazolidione compounds, polymethoxy bicyclic oxazolidine, and mixtures thereof;
   (3) a composition wherein either:
      (a) said perfume is present at a level of from about 0.003% to about 0.3%, by weight of the composition;
      (b) said composition additionally comprises a metallic salt selected from the group consisting of water-soluble zinc salts, water-soluble copper salts, and mixtures thereof; or
      (c) said composition additionally comprises low molecular weight polyols, wherein said ratio of polyol to cyclodextrin is from about 3:1,000 to about 15:100.

2. The composition of claim 1 wherein said cyclodextrin is selected from the group consisting of derivatised beta-cyclodextrins, alpha-cyclodextrin or its derivatives, gamma-cyclodextrin or its derivatives, and mixtures thereof.

3. The composition of claim 2 wherein said cyclodextrin derivatives are selected from the group consisting of methyl substituted cyclodextrins, ethyl substituted cyclodextrins, hydroxyalkyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, and mixtures thereof.

4. The composition of claim 2 wherein said cyclodextrin is selected from the group consisting of alpha-cyclodextrin, methylated alpha-cyclodextrin, methylated beta-cyclodextrin, hydroxyethyl alpha-cyclodextrin, hydroxyethyl beta-cyclodextrin, hydroxypropyl alpha-cyclodextrin, hydroxypropyl beta-cyclodextrin, and mixtures thereof.

5. The composition of claim 4 wherein said cyclodextrin is methylated beta-cyclodextrin.

6. The composition of claim 4 wherein said cyclodextrin is a mixture of methylated alpha-cyclodextrin and methylated beta-cyclodextrin.

7. The composition of claim 4 wherein said cyclodextrin is hydroxypropyl beta-cyclodextrin.

8. The composition of claim 4 wherein said cyclodextrin is a mixture of hydroxypropyl alpha-cyclodextrin and hydroxypropyl beta-cyclodextrin.

9. The composition of claim 1 wherein said cyclodextrin is present at a level of from about 0.2% to about 4%, by weight of the composition and said preservative is present at a level of from about 0.0001% to about 0.5%, by weight of the composition.

10. The composition of claim 9 wherein said cyclodextrin is present at a level of from about 0.3% to about 3%, by weight of the composition and said preservative is present at a level of from about 0.0002% to about 0.2%, by weight of the composition.

11. The composition of claim 10 wherein said cyclodextrin is present at a level of from about 0.4% to about 2%, by weight of the composition and said preservative is present at a level of from about 0.0003% to about 0.1%, by weight of the composition.

12. A stable, aqueous odor absorbing composition, for use on inanimate surfaces, comprising:
   A. from about 0.01% to about 5%, by weight of the composition, of a solubilized, water-soluble, uncomplexed cyclodextrin;
   B. an effective amount of a solubilized, water-soluble, antimicrobial preservative having a water solubility of greater than about 0.3%;
   C. optional perfume; and
   D. aqueous carrier; and
   wherein said composition is essentially free of any material that would soil or stain fabric and has a pH of greater than about 3, wherein said preservative is selected from the group consisting of organic sulfur compounds, halogenated compounds, cyclic organic nitrogen compounds, low molecular weight aldehydes, quaternary compounds, phenyl and phenoxy compounds, and mixtures thereof.

13. The composition of claim 12 wherein said preservative is an organic sulfur compound selected from the group consisting of 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; 2-methyl-4-isothiazolin-3-one; 5-chloro-2-methyl-3-isothiazolone; and mixtures thereof.

14. The composition of claim 13 wherein said preservative is a mixture of 5-chloro-2-methyl-4-isothiazolin-3-one and 2-methyl-4-isothiazolin-3-one present at a level of from about 0.0001% to about 0.01%, by weight of the composition.

15. The composition of claim 12 wherein said preservative is a halogenated compound selected from the group consisting of 5-bromo-5-nitro-1,3-dioxane; 2-bromo-2-nitropropane-1,3-diol; 1,1'-hexamethylene bis(5-(p-chlorophenyl)biguanide); and mixtures thereof.

16. The composition of claim 15 wherein said preservative is 2-bromo-2-nitropropane-1,3-diol, present at a level of from about 0.002% to about 0.1%, by weight of the composition.

17. The composition of claim 12 wherein said preservative is a cyclic organic nitrogen compound selected from the group consisting of imidazolidinedione compounds, polymethoxy bicyclic oxazolidine, and mixtures thereof.

18. A stable, aqueous odor absorbing composition, for use on inanimate surfaces, comprising:
   A. from about 0.01% to about 5%, by weight of the composition, of a solubilized, water-soluble, uncomplexed cyclodextrin;

B. an effective amount of a solubilized, water-soluble, antimicrobial preservative having a water solubility of greater than about 0.3%;

C. optional perfume; and

D. aqueous carrier; and wherein said composition is essentially free of any material that would soil or stain fabric and has a pH of greater than about 3, wherein said perfume is present at a level of from about 0.003% to about 0.3%, by weight of the composition.

19. The composition of claim 18 wherein said perfume is present at a level of from about 0.005% to about 0.2%, by weight of the composition.

20. A stable, aqueous odor absorbing composition, for use on inanimate surfaces, comprising:
  A. from about 0.01% to about 5%, by weight of the composition, of a solubilized, water-soluble, uncomplexed cyclodextrin;
  B. an effective amount of a solubilized, water-soluble, antimicrobial preservative having a water solubility of greater than about 0.3%;
  C. optional perfume; and
  D. aqueous carrier; and wherein said composition is essentially free of any material that would soil or stain fabric; has a pH of greater than about 3, and additionally comprises a metallic salt selected from the group consisting of water-soluble zinc salts, water-soluble copper salts, and mixtures thereof.

21. The composition of claim 20 wherein said metallic salt is selected from the group consisting of $ZnCl_2$, $CuCl_2$, and mixtures thereof.

22. The composition of claim 21 wherein said metallic salt is $ZnCl_2$, present at a level of from about 0.1% to about 10%, by weight of the composition.

23. A stable, aqueous odor absorbing composition, for use on inanimate surfaces, comprising:
  A. from about 0.01% to about 5%, by weight of the composition, of a solubilized, water-soluble, uncomplexed cyclodextrin;
  B. an effective amount of a solubilized, water-soluble, antimicrobial preservative having a water solubility of greater than about 0.3%;
  C. optional perfume; and
  D. aqueous carrier; and wherein said composition is essentially free of any material that would soil or stain fabric; has a pH of greater than about 3, and additionally comprises low molecular weight polyols, wherein the ratio of polyol to cyclodextrin is from about 3:1,000 to about 15:100.

24. The composition of claim 23 wherein said low molecular weight polyol is propylene glycol, ethylene glycol, glycerol, and mixtures thereof.

25. A stable, aqueous odor absorbing composition, for use on inanimate surfaces, comprising:
  A. from about 0.01% to about 5%, by weight of the composition, of a solubilized, water-soluble, uncomplexed cyclodextrin;
  B. an effective amount of a solubilized, water-soluble, antimicrobial preservative having a water solubility of greater than about 0.3%;
  C. optional perfume; and
  D. aqueous carrier; and wherein said composition is essentially free of any material that would soil or stain fabric; has a pH of greater than about 3, and additionally comprises a chelating agent present at a level of from about 0.01% to about 0.3%, by weight of the composition.

26. A stable, aqueous odor absorbing composition, for use on inanimate surfaces, comprising:
  A. from about 0.5% to about 5%, by weight of the composition, of a mixture of methylated beta-cyclodextrin and alpha-cyclodextrin;
  B. from about 0.0001% to about 0.01%, by weight of the composition, of a solubilized, water-soluble, antimicrobial preservative comprising a mixture of 5-chloro-2-methyl-4-isothiazolin-3-one and 2-methyl-4-isothiazolin-3-one;
  C. from about 0.003% to about 0.3%, by weight of the composition, of perfume;
  D. from about 0.05% to about 1%, by weight of the composition, of solubilizing aid;
  E. from about 0.05% to about 10%, by weight of the composition, of antistatic agent; and
  F. water; and wherein said composition is essentially free of any material that would soil or stain fabric and has a pH greater than about 4.

27. A stable, aqueous odor absorbing composition, for use on inanimate surfaces, comprising:
  A. from about 0.5% to about 2%, by weight of the composition, of a mixture of methylated alpha-cyclodextrin and methylated beta-cyclodextrin;
  B. from about 0.0002% to about 0.005%, by weight of the composition of solubilized, water-soluble, antimicrobial preservative comprising a mixture of 5-chloro-2-methyl-4-isothiazolin-3-one and 2-methyl-4-isothiazolin-3-one;
  C. from about 0.005% to about 0.2%, by weight of the composition, of perfume; and
  D. water; and wherein said composition is essentially free of any material that would soil or stain fabric and has a pH of greater than about 4.

28. A stable, aqueous odor absorbing composition, for use on inanimate surfaces, comprising:
  A. from about 0.5% to about 2%, by weight of the composition, a mixture of alpha-cyclodextrin and hydroxypropyl beta-cyclodextrin;
  B. from about 0.0003% to about 0.003%, by weight of the composition, of solubilized, water-soluble, antimicrobial preservative comprising a mixture of 5-chloro-2-methyl-4-isothiazolin-3-one and 2-methyl-4-isothiazolin-3-one;
  C. from about 0.005% to about 0.2%, by weight of the composition, of a perfume;
  D. from about 0.3% to about 5%, by weight of the composition, of $ZnCl_2$; and
  E. water; and wherein said composition is essentially free of any material that would soil or stain fabric and has a pH of from about 4 to about 5.5.

29. A stable, aqueous odor absorbing composition, for use on inanimate surfaces, comprising:
  A. from about 0.5% to about 2%, by weight of the composition, of a mixture of alpha-cyclodextrin and hydroxypropyl beta-cyclodextrin;
  B. from about 0.0001% to about 0.01%, by weight of the composition of solubilized, water-soluble, antimicrobial preservative comprising a mixture of 5-chloro-2-methyl-4-isothiazolin-3-one and 2-methyl-4-isothiazolin-3-one;

C. propylene glycol present at a polyol-to-cyclodextrin weight ratio of from about 3:1000 to about 15:100; and D. water; and wherein said composition is essentially free of any material that would soil or stain fabric and has a pH of greater than about 4.

30. A stable, aqueous odor absorbing composition, for use on inanimate surfaces, comprising:

A. from about 0.5% to about 2% of a mixture of hydroxypropyl alpha-cyclodextrin and hydroxypropyl beta-cyclodextrin;

B. from about 0.0001% to about 0.01% of solubilized, water-soluble, antimicrobial preservative comprising a mixture of 5-chloro-2-methyl-4-isothiazolin-3-one and 2-methyl-4-isothiazolin-3-one;

C. from about 0.3 to about 5%, by weight of the composition, of $ZnCl_2$;

D. propylene glycol present in a polyol-to-cyclodextrin weight ratio of from about 3:1000 to about 15:100;

E. from about 0.005% to about 0.2%, by weight of the composition, of perfume; and F. water; and wherein said composition is essentially free of any material that would soil or stain fabric and has a pH of from about 4 to about 5.5.

31. A stable, aqueous odor absorbing composition, for use on inanimate surfaces, comprises:

A. from about 0.01% to about 5%, by weight of the composition, of a solubilized, water-soluble, uncomplexed cyclodextrin;

B. an effective amount of a solubilized, water-soluble, antimicrobial preservative having a water solubility of greater than about 0.3%;

C. a material selected from the group consisting of:
  1. perfume at a level of from about 0.003% to about 0.3%, by weight of the composition;
  2. metallic salt selected from the group consisting of water-soluble zinc salts, water-soluble copper salts, and mixtures thereof;
  3. low molecular weight polyols, wherein the ratio of polyol to cyclodextrin is from about 3:1,000 to about 15:100.
  4. chelating agent at a level of from about 0.01% to about 0.3%, by weight of the composition; and
  5. mixtures thereof; and D. aqueous carrier; and wherein said composition is essentially free of any material that would soil or stain fabric and has a pH of greater than about 3.

* * * * *